United States Patent [19]

Nishimura et al.

[11] Patent Number: 5,122,381
[45] Date of Patent: Jun. 16, 1992

[54] COMPOSITION AND PROCESS FOR DISSOLVING A SPARINGLY WATER-SOLUBLE FLAVONOID

[75] Inventors: Masato Nishimura; Hiroshi Horikawa; Masamitsu Moriwaki, all of Osaka, Japan

[73] Assignee: San-Ei Chemical Industries, Ltd., Osaka, Japan

[21] Appl. No.: 570,305

[22] Filed: Aug. 20, 1990

[30] Foreign Application Priority Data

Aug. 21, 1989 [JP] Japan ................ 1-215788

[51] Int. Cl.⁵ .............................. A23L 00/00
[52] U.S. Cl. .................... 426/654; 426/262; 426/321; 426/590; 426/650
[58] Field of Search ........... 426/654, 262, 321, 590, 426/650

[56] References Cited

U.S. PATENT DOCUMENTS 3,832,475  8/1974  Zirlin .................. 426/590

FOREIGN PATENT DOCUMENTS 032073  10/1979  Japan .

OTHER PUBLICATIONS

Chemical Abstracts, vol. 40, 8334i, Rutin solution for injection.
Chemical Abstracts, 1953, 834d, Water-soluble rutin compound.
Chemical Abstracts, 1955, 574a, Water-soluble rutin compounds.
Chemical Abstracts, vol. 79, p. 481, 66751h, 1973, Water-soluble derivatives of vitamin P.

*Primary Examiner*—Donald E. Czaja
*Assistant Examiner*—Leslie Wong
*Attorney, Agent, or Firm*—Sandler, Greenblum & Bernstein

[57] ABSTRACT

A process for dissolving a sparingly water-soluble flavonoid in an aqueous medium by use of one or more kinds of quercetin-3-0-glycosides, which is applicable to the case of using the sparingly water-soluble flavonoid as an antifading agent for colored drinks.

13 Claims, 2 Drawing Sheets

COMPOSITION AND PROCESS FOR DISSOLVING A SPARINGLY WATER-SOLUBLE FLAVONOID

BACKGROUND OF THE INVENTION

1. Field of the Invention

The present invention relates to a process for dissolving a sparingly water-soluble flavonoid.

2. Prior Art

Rutin, which is one of the typical sparingly water-soluble flavonoids, has pharmacological actions such as antioxidizing action, blood vessel reinforcing action and the like. Alternatively, rutin has been frequently used as an antifading agent for colored drinks. Where rutin is used as the antifading agent, it is desirable that at least about 0.01 W/V% of rutin be present in the aqueous solution. However, rutin is sparingly water-soluble, and its solubility is about 0.008 % in water at an ordinary temperature.

Some methods for dissolving rutin in water for pharmaceutical purpose are known, i.e., adding an aliphatic compound having an amino group to rutin (Japanese Published Examined Patent Application No. 1677/1950), and allowing a halogenated acetic acid or Rongalite to act on rutin for improving in its water-solubility (Japanese Published Examined Patent Application No. 2724/1951; No. 1285/1954).

Further, Japanese Published Examined Patent Application No. 32073/1979 has disclosed that reacting rutin with dextrin in the presence of transglycosidase gives a water-soluble product (a mixture of rutin, rutinglycoside, rutinmaltoside and rutinmaltotrioside).

However, it is not known that adding a small amount of a flavonoid analog to rutin improves the water-solubility of rutin.

In the case of using a sparingly water-soluble flavonoid such as rutin as an antifading agent for colored drinks, a method for dissolving the sparingly water-soluble flavonoid has been desired such that an antifading property of the agent is not affected, hygienic chemical problems do not arise in drinking, and a small amount of a dissolution enhancing agent can improve the water-solubility of the flavonoid to a desired degree.

SUMMARY OF THE INVENTION

Accordingly, the present invention provides a process for dissolving a sparingly water-soluble flavonoid which comprises dissolving a sparingly water-soluble flavonoid in an aqueous medium in the presence of at least one kind of quercetin-3-0-glycoside of the formula (I):

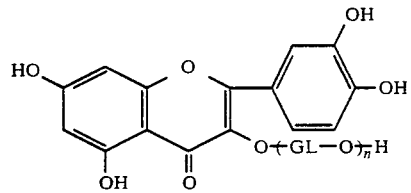

where GL is a glucose residue, and n is an integer of 1 or more.

DETAILED DESCRIPTION OF THE PREFERRED EMBODIMENT

Figure 1:
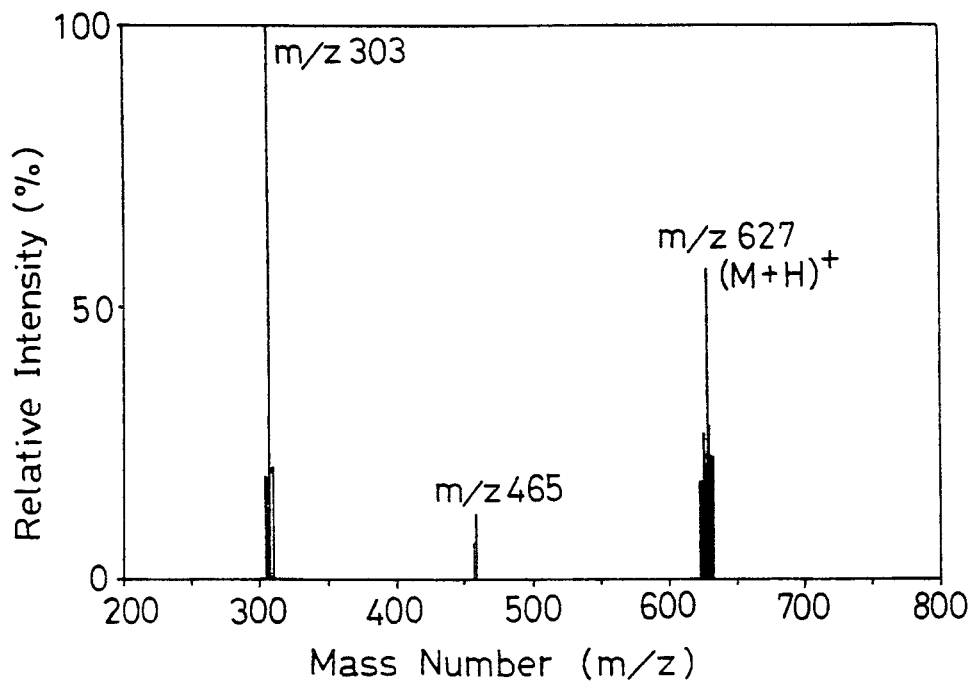
FIGS. 1(a) and 1(b) are mass spectra of respective quercetin-3-0-glycosides of the formula (I) where n=2 and n=3, which are obtained in Example of the invention.
Figure 1:
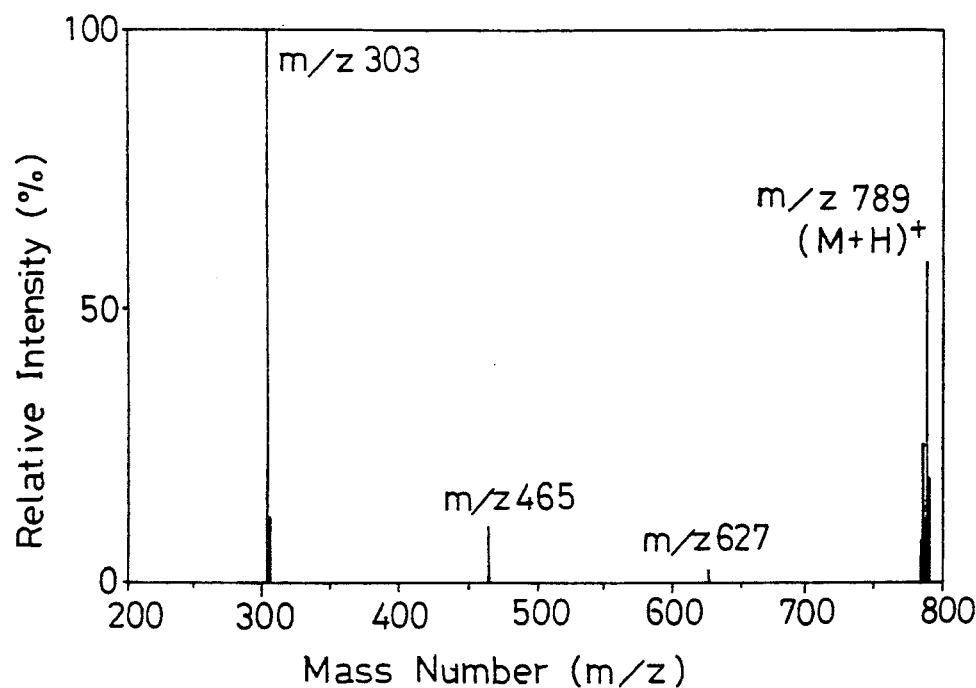

The term "sparingly water-soluble flavonoid" in the invention is meant by rutin or its analog including quercetin, morin and the like.

The compound of the formula (I) is usually used in 13–25 wt. %, preferably 17–25 wt. % to the sparingly water-soluble flavonoid. The use the compound (I) within the above range will give a stable solution containing 0.01–0.04 W/V% of the sparingly water-soluble flavonoid stably soluble in an aqueous medium.

The term "aqueous medium" in the invention is meant by water or water containing one or more solutes, for example, carbon dioxide gas, a fruit juice, sugar, a coloring agent, a flavor, an organic acid, a vitamin, an extract of animals or plants and the like.

The compound of the formula (I) can be obtained by reacting quercetin-3-0-monoglucoside as a source material which is converted from rutin by an enzyme like naringinase with a glucose source in the presence of a glucose residue transferase such as glycosidase or transglycosidase for transferring equimolar or more quantity of glucose residue.

As the above glucose source, any glucose source of which one or more glucosyl residues can be transferred to a quercetin-3-0-monoglucoside molecule can be used, for example, amylose, amylopectin, a starch, a liquefied starch, a saccharified starch, cyclodextrin and the like. The glucose is usually used in about 50–1000 wt. %, advantageously about 100–400 wt. %, relative to quercetin-3-0-monoglucoside.

Examples of the above glycosidases are c-amylase (E.C.3.2.1.1.) and α-glucosidase (E.C.3.2.1.20). Examples of the above transglycosidases are cyclodextrin-glucanotransferase (E.C.2.4.1.19) (hereinafter abbreviated as CGT-ase) and the like.

It is known that CGT-ase is produced by a bacteria of Bacillus strain such as Bacillus circulans, Bacillus macerans, Bacillus stearothermophilus, Bacillus megatherium, Bacillus polymyxa and the like, or of Klebsiella strain such as Klebsiella pneumoniae and the like. CGT-ase produced by any of the above bacteria can be used and is not necessarily required to be purified, usually it is used in a crude enzyme state. Alternatively, an enzyme on market such as CONTIZYME (trademark of AMANOSEIYAKU Co., Ltd.) may be used. Otherwise, instead of adding CGT-ase, CGT-ase producing bacteria is inoculated into a culture solution including quercetin-3-0-monoglucoside and the glucose source to cause glycosyl transfer reaction by means of fermentation. Further, immobilized CGT-ase producing bacteria can be used to cause glycosyl transfer reaction.

In this reaction system, it is advantageous that pH is about 11 or less, especially 9-2. In order to improve reaction conditions of quercetin-3-0-monoglucoside, unreacted rutin, remaining naringinase and generated rhamnose may be eliminated. Where enzyme activity of CGT-ase is about 600 units, an amount thereof to be added is usually about 100 wt. % or less, preferably about 60–10 wt. % relative to an amount of the glucose source to be used.

The resultant thus obtained is a mixture of quercetin-3-0-glycoside in which equimolar or more quantity of glucose is further bonded to the glucose residue of quercetin-3-0-monoglucoside, and which usually contains unreacted quercetin-3-0-monoglucoside, an amount of the unreacted quercetin-3-0-monoglucoside being dependent on reaction conditions thereof. For better dissolution of rutin in water, especially preferable is quercetin-3-0-glycoside of the formula (I) where n is 2-8. However, quercetin-3-0-glycoside of the formula (1) where n is 2 or more may be used. Otherwise, using a quercetin-3-0-glycoside mixture containing unreacted quercetin-3-0-monoglucoside can achieve the object of the invention.

Hereinafter, the present invention will be more fully described with reference to an example which is not limitative to the invention.

EXAMPLE

EXAMPLE 1

Preparation of the compound of the formula (I)

Rutin (5 g) was dispersed in 1 l of water at 55 °C., to which 1 g of naringinase [naringinase "AMANO" (trademark of AMANOSEIYAKU Co., Ltd.)] was added. This mixture showed pH 7. The mixture was maintained at 50 °C. for 5 hours, thereafter concentrated to give 0.5 l of concentrate. Quercetin-3-0-monoglucoside was precipitated when the concentrate was cooled. Precipitated quercetin-3-0-monoglucoside was separated, to which 0.2 l of water and 8 g of cornstarch were added. This mixture was made homogeneous, then added with 2 ml of CGT-ase [CONTIZYME (trademark of AMANOSEIYAKU Co., Ltd.)] and maintained at 45 °C. for 12 hours (pH 6). The mixture was concentrated to give 20 g of concentrate.

This concentrate was separated into each component by a high-speed liquid chromatograph (HPLC of NIPPON BUNKOH KABUSHIKIKAISHA, type: TRI ROTAR-V), which was subsequently analyzed by a mass spectrograph (MS of Hitachi, Ltd., type: M-80B, a part of this analysis is shown in FIG. 1) and a nuclear magnetic resonance apparatus (NMR of JEOL, LTD., type: FX-200). According to the above analysis, the concentrate turned out to be a mixture of quercetin-3-0-glycoside containing 24 mol% of unreacted quercetin-3-0-monoglucoside and the following compounds of the formula (I): Compound (n=2): 23 mol%, Compound (n=3): 17 mol%, Compound (n=4): 12 mol%, Compound (n=5): 9 mol%, Compound (n=6): 7 mol%, Compound (n=7): 4 mol%, Compound (n=8): 2 mol%, and Compound (n=9-11): 2 mol%.

This glycoside mixture will hereinafter be termed as Glycoside I. Mass spectra of the compounds (n=2 and n=3) are shown in FIGS. 1(a) and 1(b), respectively.

Dissolution of Rutin

Water (100 ml) containing 12 W/V% of granulated sugar and 0.3 W/V% of citric acid was poured into each of five test tubes (100 ml) No. 1 to 5, to which 0.4 ml of rutin (10 W/V%) solution in ethanol (equivalent to 0.04 g of rutin) was added. Immediately thereafter, mixed was a solution of the Glycoside I (13.4 W/V%) in ethanol in amounts of 0.024 ml, 0.032 ml, 0.04 ml and 0.05 ml respectively to the test tubes No. 2 to 5. These amounts were equivalent to 8.0 wt. %, 10.8 wt. %, 13.5 wt. % and 16.0 wt. %, respectively relative to the amount of rutin.

All of these mixtures including No. 1 to which the Glycoside I had not been added were transparent when observed immediately after mixing. After standing for 24 hours, some mixtures were recognized to have precipitation. Standing was continued for 14 days at room temperature in observing precipitation states of the mixtures. On completion of this standing, rutin concentration of each supernatant liquid of the mixtures was measured using high-speed liquid chromatography. The result of this measurement is shown in the following Table 1.

TABLE 1

| No. | 1 | 2 | 3 | 4 | 5 |
|---|---|---|---|---|---|
| Initial Concentration of Rutin (wt %) | 0.04 | 0.04 | 0.04 | 0.04 | 0.04 |
| Amount of Glycoside I [concentration in aqueous solution (wt %)] | 0 | 0.0032 | 0.0043 | 0.0054 | 0.0064 |
| Amount of Glycoside I relative to Rutin (wt %) | 0 | 8.0 | 10.8 | 13.5 | 16.0 |
| Precipitation Observed | | | | | |
| 1st day | + + | + | — | — | — |
| 3rd day | + + | + | ± | — | — |
| 6th day | + + | + | ± | — | — |
| 14th day | + + | + | ± | — | — |

Note: + means that precipitation was observed.
— means that precipitation was not observed.

The "+" and "—" signs in Table 1 denote comparative amounts of precipitation of the rutin. The range extends from "+ +", indicating the greatest degree of precipitation, down to "—", indicating no observed precipitation.

Figure 2:
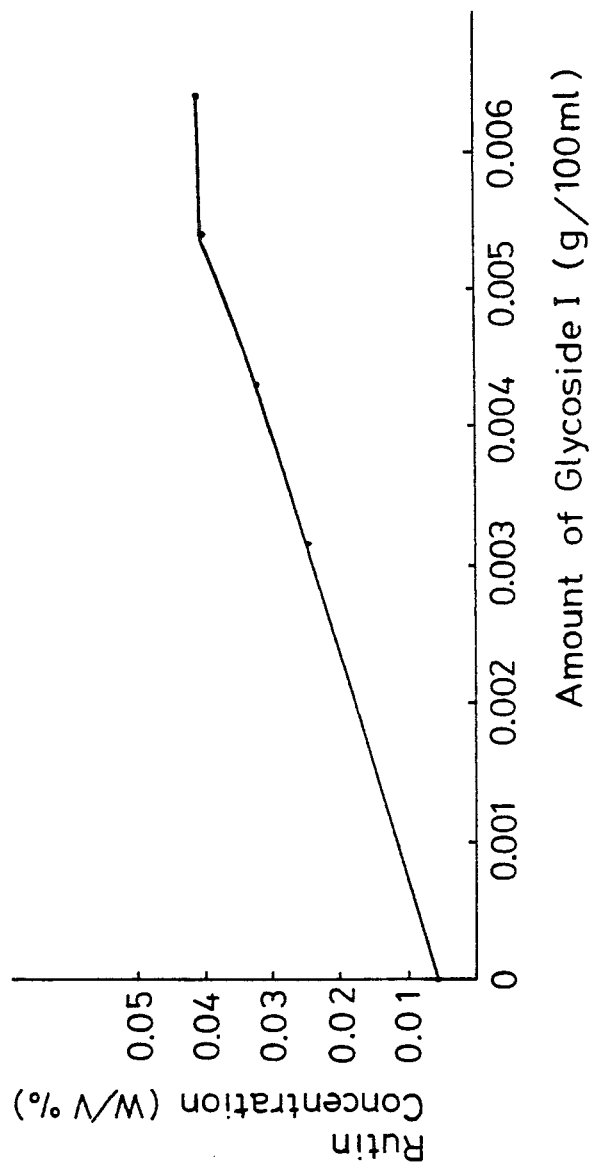
FIG. 2 is a graph showing a solubility of rutin relative to a concentration of quercetin-3-0-glycoside obtained in Example of the invention.

Further regarding the solubility of rutin, as affected by the amount of Glycoside I present, the x-axis of the graph in FIG. 2 shows the amounts of Glycoside I added to each of test tubes 2-5, as shown in Table 1. The y-axis of this graph shows the amount of rutin remaining in solution for each of test tubes 1-5.

As shown in Table 1 and FIG. 2, it was confirmed that at least 0.04 wt. % of rutin is stably dissolved in water by adding 13.5 wt. % of Glycoside I relative to the amount of rutin used.

According to the present invention, quercetin-3-0-glycoside in which equimolar or more quantity of glucose is further bonded to a glucose residue of quercetin-3-0-monoglucoside makes it possible to enhance the solubility of a sparingly water-soluble flavonoid in an aqueous medium.

Further according to the present invention, in the case of using a sparingly water-soluble flavonoid such as rutin as an antifading agent for colored drinks, a method for dissolving a sparingly water-soluble flavonoid can be provided such that an antifading property of the agent is not affected, hygienic chemical problems do not arise in drinking, and a small amount of a dissolution enhancing agent can improve the water-solubility of the flavonoid to a desired degree.

What is claimed is:

1. A process for dissolving a sparingly water-soluble flavonoid which comprises dissolving a sparingly water-soluble flavonoid in an aqueous medium in the presence of at least one kind of quercetin-3-0-glycoside of the formula (I):

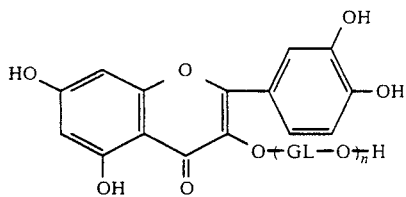

where GL is a glucose residue, and n is an integer of 1 or more.

2. The process as set forth in claim 1, wherein 13–25 wt. % of the quercetin-1-0-glycoside (I) is used relative to the amount of the sparingly water-soluble flavonoid to be used.

3. The process as set forth in claim 1, wherein the sparingly water-soluble flavonoid is rutin.

4. The process as set forth in claim 1, wherein the quercetin-3-0-glycoside (I) is obtained by reaction of quercetin-3-0-monoglucoside with a glucose source in the presence of a glycosidase or a transglycosidase.

5. The process as set forth in claim 3, wherein rutin is dissolved at 0.01–0.04 W/V% in the aqueous medium.

6. The process as set forth in claim 1, wherein n is 2–8.

7. The process as set forth in claim 4, wherein 50–1000 wt. % of glucose is used relative to the amount of the quercetin-3-O-monoglucoside to be used.

8. The process as set forth in claim 4, wherein the reaction is conducted at a pH of about 11 or less.

9. A solution comprising:
  (a) an aqueous medium;
  (b) a sparingly water-soluble flavonoid; and
  (c) at least one quercetin-3-O-glycoside of the formula

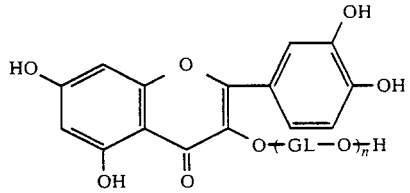

where GL is a glucose residue, and n is an integer of 1 or more.

10. The solution as set forth in claim 9, wherein n is 2–8.

11. The solution as set forth in claim 9, comprising 13–25 wt. % of the quercetin, relative to the amount of the sparingly water-soluble flavonoid.

12. The solution as set forth in claim 9, wherein the sparingly water-soluble flavonoid is rutin.

13. The solution as set forth in claim 12, comprising 0.01–0.04 W/V% of the rutin in the aqueous medium.

* * * * *